US006207866B1

(12) United States Patent
Kawamata et al.

(10) Patent No.: US 6,207,866 B1
(45) Date of Patent: Mar. 27, 2001

(54) METHOD FOR PRODUCING DIARYLMETHANE OR ITS DERIVATIVES

(75) Inventors: Tadanori Kawamata, Kawasaki; Hideyuki Dohi, Yokohama; Satoru Inoue, Chigasaki; Shozo Hayashi, Yokohama, all of (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/111,873

(22) Filed: Jul. 8, 1998

(30) Foreign Application Priority Data

Jul. 11, 1997 (JP) ................................................... 9-202130
Jul. 11, 1997 (JP) ................................................... 9-202131

(51) Int. Cl.$^7$ .................................................. C07C 39/16
(52) U.S. Cl. ........................... 568/723; 585/25; 585/469
(58) Field of Search ........................... 568/723; 585/25, 585/469

(56) References Cited

U.S. PATENT DOCUMENTS

| | | |
|---|---|---|
| Re. 29,857 | 12/1978 | Argauer et al. . |
| Re. 32,162 | 5/1986 | Sato et al. . |
| 1,908,190 | 5/1933 | Scholkopf . |
| 2,282,327 | 5/1942 | Dreisbach . |
| 2,981,765 | 4/1961 | Fetterly . |
| 3,043,886 | 7/1962 | Serres, Jr. et al. . |
| 3,248,339 | 4/1966 | Spes et al. . |
| 3,702,886 | 11/1972 | Argauer et al. . |
| 3,709,979 | 1/1973 | Chu . |
| 3,758,403 | 9/1973 | Rosinski et al. . |
| 3,786,107 | 1/1974 | Kuribayashi et al. . |
| 3,790,471 | 2/1974 | Argauer et al. . |
| 3,832,449 | 8/1974 | Rosinski et al. . |
| 3,836,383 | 9/1974 | Kiritani et al. . |
| 3,926,782 | 12/1975 | Plank et al. . |
| 3,936,566 | 2/1976 | Sato et al. . |
| 3,965,209 | 6/1976 | Butter et al. . |
| 4,011,278 | 3/1977 | Plank et al. . |
| 4,035,285 | 7/1977 | Owen et al. . |
| 4,111,825 | 9/1978 | Schulz et al. . |
| 4,117,026 | 9/1978 | Haag et al. . |
| 4,219,687 | 8/1980 | Dolhyj et al. . |
| 4,228,024 | 10/1980 | Schulz et al. . |
| 4,289,806 | 9/1981 | Sato et al. . |
| 4,306,106 | 12/1981 | Kerr et al. . |
| 4,365,103 | 12/1982 | Chang et al. . |
| 4,454,364 | 6/1984 | Farcasiu et al. . |
| 4,463,209 | 7/1984 | Kursewicz et al. . |
| 4,476,330 | 10/1984 | Kerr et al. . |
| 4,523,044 | 6/1985 | Commandeur et al. . |
| 4,642,730 | 2/1987 | Sato et al. . |
| 4,681,980 | 7/1987 | Sato et al. . |
| 4,686,548 | 8/1987 | Takahashi et al. . |
| 4,870,221 | 9/1989 | Sato et al. . |
| 4,895,988 | 1/1990 | Clerici et al. . |
| 4,899,009 | 2/1990 | Kawakami et al. . |
| 4,902,841 | 2/1990 | Kawakami et al. . |
| 4,982,025 | 1/1991 | Kawakami et al. . |
| 5,068,481 | 11/1991 | Akatsi et al. . |
| 5,073,655 | 12/1991 | Angevine et al. . |
| 5,171,906 | 12/1992 | Kawakami et al. . |
| 5,877,362 | 3/1999 | Dohi et al. .............................. 585/25 |
| 5,880,322 | 3/1999 | Dohi et al. ............................ 585/469 |

FOREIGN PATENT DOCUMENTS

| | | |
|---|---|---|
| 1475973 | 6/1977 | (GB) . |
| 1555728 | 11/1979 | (GB) . |
| 46-10064 | 3/1971 | (JP) . |
| 62-41656 | 9/1983 | (JP) . |
| 1-180835 | 7/1989 | (JP) . |
| 02134332 | 5/1990 | (JP) . |

OTHER PUBLICATIONS

Yamada et al., "Catalytic Decomposition of 1,1–diphenylethane," J. Chem. Soc. Jpn., Ind., Chem. Sect., 72, [7] (1969), pp. 1512–1515 (Abstract Only).

Walker, J., "Formaldehyde," ACS Monograph Series, Reinhold Publishing Corp., New York, pp. 436–437 (Year Not Available).

Climent et al, "Condensation of Formaldehyde with Benzene in the Presence HY Zeolites," Applied catalysis, 51 (1989) pp. 113–125.

*Primary Examiner*—Laura L. Stockton

(57) ABSTRACT

A method to produce diarylmethane or its derivatives by condensation reaction can be carried out without difficulty and without the deterioration of catalyst, and the intended product can be produced inexpensively by recovering and recycling used alcohol. In the method, dimethoxymethane and an aromatic compound are reacted at a temperature of 80 to 400° C. with an acid catalyst. Further, the method comprises the steps of (1) reacting alcohol with formaldehyde using an acid catalyst to obtain acetal; (2) reacting the acetal and an aromatic compound using an acid catalyst to obtain a reaction mixture containing diarylmethane or its derivatives and alcohol; (3) separating and recovering diarylmethane or its derivatives and alcohol from the reaction mixture, and (4) recycling at least a portion of the recovered alcohol to the step (1).

24 Claims, 1 Drawing Sheet

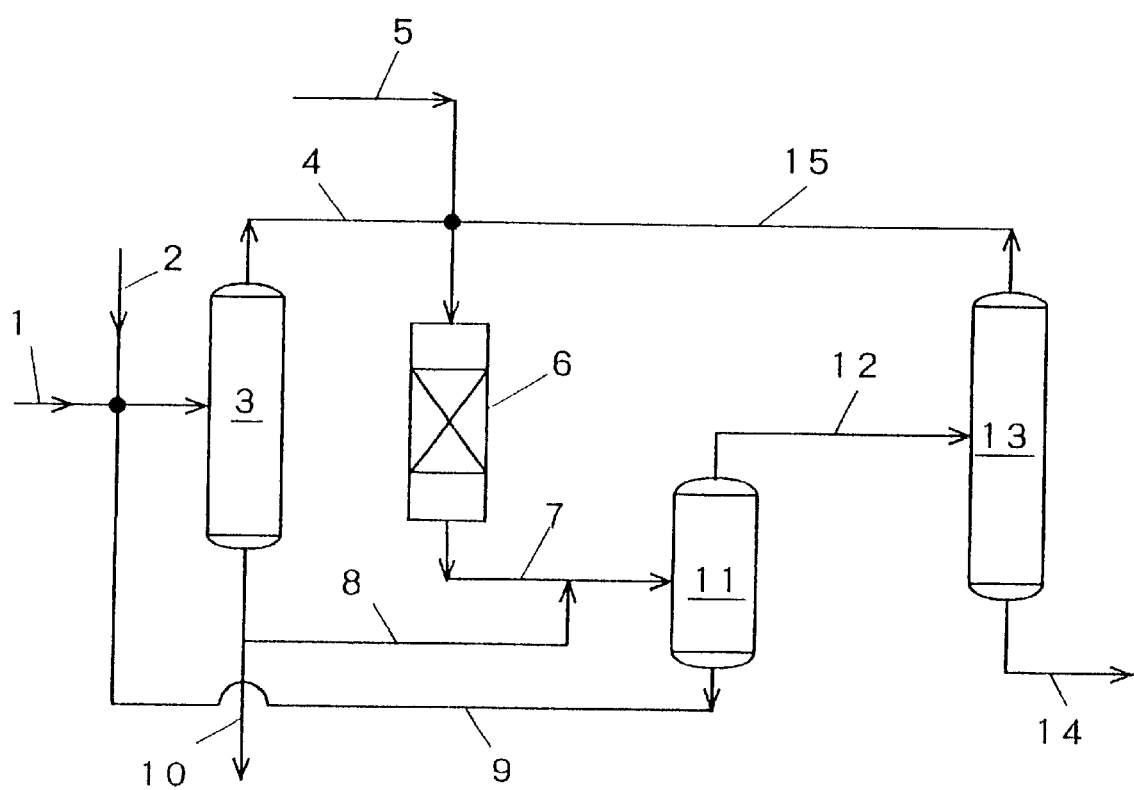

METHOD FOR PRODUCING DIARYLMETHANE OR ITS DERIVATIVES

BACKGROUND OF THE INVENTION (1) Field of the Invention

This invention relates to a method for producing diarylmethane or its derivatives which are useful as high boiling point aromatic solvents and intermediate compounds for producing various kinds of chemical substances. More particularly, the invention relates to a method for producing diarylmethane or its derivatives from easily available compounds of simple structure such as alcohol, formaldehyde and aromatic compounds.

(2) Prior Art

As the methods for producing the diarylmethane, it is proposed to condense aromatic compounds with several condensing agents. For example, it is proposed that various condensing agents such as halogenated hydrocarbon, formaldehyde or its aqueous solution as formalin are condensed with aromatic compounds in the presence of a catalyst.

A method to use formaldehyde or its aqueous solution of formalin as a condensing agent is preferable because they are inexpensive. In this method, water is generated as a result of condensation. So that, it is not desirable because a by-product water sometimes impairs the activity of acid catalyst or it dilutes the catalyst. For example, in the methods disclosed in J. Frederic Waker, FORMALDEHYDE, 3rd Ed.; U.S. Pat. Nos. 3,043,886; and 2,981,765; and Japanese Laid-Open Patent Publication No. 2-134332, the condensation reaction of aromatic hydrocarbons is carried out using formaldehyde as a condensing agent and sulfuric acid or aluminum chloride as a catalyst. In examples in the above disclosure, when a catalyst such as sulfuric acid or aluminum chloride is used, the subsequent treatment for used catalyst is difficult, in addition, even when adequate reaction conditions are employed, highly condensed products having three or more benzene rings are undesirably produced in addition to an intended product.

The reaction of condensation using a condensing agent of formaldehyde and a solid acid catalyst of zeolite is disclosed in Applied Catalysis, 51, 113–115 (1989); U.S. Pat. Nos. 4,011,278; 4,306,106; 4,476,330; and 4,895,988; and Japanese Laid-Open Patent Publication No. 1-180835. In the reaction disclosed in these references, although the dilution of catalyst owing to by-product water is not caused because solid acid catalysts are used, the lowering of catalytic activity cannot be avoided. Furthermore, the condensation using a condensing agent of formalin as an aqueous solution of formaldehyde in the presence of zeolite catalyst is disclosed in the foregoing U.S. Pat. No. 4,895,988 and Japanese Laid-Open Patent Publication No. 1-180835. In these cases, the catalytic activity is not satisfactory because the condensation is done in the presence of water from the beginning stage. Accordingly, in these examples, the condensation of reactive phenol is mainly done.

Furthermore, several methods of condensation using halogenated hydrocarbons as condensing agents are well known in the prior art. Some of them are put into industrial practice. The by-products of halogenated hydrocarbons have not especially undesirable influence on the condensation reaction. However, the method involves several problems caused by the by-product hydrogen halide, such as the troubles in after-treatment, remained chlorine in the obtained product, and corrosion of apparatus. Furthermore, the problem concerning the polyhalogenated aromatic compounds produced by side reactions is posed recently.

In view of the above-described state of prior art to produce the diarylmethane which is useful as high-boiling aromatic solvents and as intermediates for various kinds of chemical products, it is eagerly wanted to propose an industrially workable method for synthesizing diarylmethane without difficulty and on a high yield using a novel condensing agent.

By the way, it is to be noted that the term "condensing agent" herein referred to means one of reactants used in the condensation reaction and it is bifunctional in the condensation. With its bifunctional property, it can couple two molecules of aromatic hydrocarbon of the other reactant in the condensation. The number of functional groups in an aromatic hydrocarbon in the condensation reaction basically corresponds to the number of hydrogen atoms connected to the benzene ring. However, all the hydrogen atoms on the benzene ring have not always the same reaction characteristics because of the orientation.

BRIEF SUMMARY OF THE INVENTION

The present inventors have found that when acetal, such as dimethoxymethane, is used as a condensing agent, a by-product of alcohol is formed in place of the by-product of water in the condensation reaction, in which formaldehyde is used as a condensing agent. As a result, it has been made possible to carry out the reaction system of condensation substantially without the existence of water. Accordingly, it is possible to avoid the occurrence of the above discussed deterioration of catalyst and the lowering of catalyst concentration.

Furthermore, when acetal is used as a condensing agent, a by-product of alcohol is produced. However, if the alcohol is discarded, the use quantity of alcohol is inevitably increases to raise undesirably the cost for the raw material. This problem has also been solved in the present invention. In other words, when acetal is synthesized from formaldehyde and alcohol, the by-product of alcohol in the condensation reaction can be recycled to the process of acetal synthesis, thereby enhancing economical efficiency. The acetal, e.g., dimethoxymethane (methylal) does not form substantially an azeotropic mixture with water. Accordingly, it is possible to separate easily the produced acetal from by-product of water which is produced in the synthesis of acetal from formaldehyde and alcohol. As a result, it is possible to recover acetal of low water content and to carry out the condensation reaction under the condition substantially without the existence of water. In view of this advantage, it is desirable to synthesize acetal from formaldehyde and alcohol.

Accordingly, the principal object of the present invention is to provide an improved method for efficiently producing diarylmethane and its derivatives using a condensing agent through a simplified process without suffering the deterioration of catalyst.

Another object of the present invention is to provide a method for easily producing diarylmethane and its derivatives using inexpensive reactants.

A further object of the present invention is to provide a method for easily producing diarylmethane and its derivatives in high yield by recovering and recycling the by-product in the condensation process.

Accordingly, the method for producing diarylmethane and its derivatives in the present invention is characterized in that dimethoxymethane and an aromatic compound are reacted together at a reaction temperature in the range of 80 to 400° C. in the presence of an acid catalyst.

Preferable example of diarylmethane and its derivatives produced in the present invention are represented by the following general formula [I]:

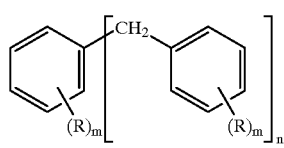

wherein m is an integer from 0 to 3, n is 1 or 2 and R is independently hydrogen atom, an alkyl group having 1 to 4 carbon atoms or a hydroxyl group.

The method for producing diarylmethane and its derivatives comprises the following steps (1) to (4) using starting materials of alcohol, formaldehyde and aromatic compound:

(1) reacting alcohol with formaldehyde in the presence of an acid catalyst to obtain acetal;

(2) reacting the acetal and an aromatic compound in the presence of an acid catalyst to obtain a reaction mixture containing diarylmethane or its derivatives and alcohol;

(3) separating and recovering diarylmethane or its derivatives, and alcohol, respectively, from the reaction mixture containing diarylmethane or its derivatives and alcohol; and (4) recycling at least a portion of the recovered alcohol to the above-mentioned step (1) to obtain acetal.

It is possible to use an aqueous solution of formaldehyde, i.e., formalin, in place of the formaldehyde itself to be used in the above step (1). In such a case, because much water exists in the reaction system, the reaction mixture containing diarylmethane or its derivatives and alcohol in the separation step (3) is extracted with water to separate an oily phase and an aqueous phase, and the diarylmethane or its derivatives are recovered from the oily phase, while alcohol is recovered from the aqueous phase.

The raw material of alcohol is typically exemplified by methanol and the aromatic compound is exemplified by benzene, toluene, phenol and cresol.

In the method of the present invention, a novel condensing agent of acetal is used in the preparation of diarylmethane or its derivatives through condensation in the presence of an acid catalyst. By using acetal as a condensing agent, the lowering of catalytic activity can be avoided effectively due to the advantageous property of the condensing agent itself and to the fact that the by-product is methanol. Therefore, the yield of preparation of diarylmethane or its derivatives is much improved as compared with the conventional methods.

BRIEF DESCRIPTION OF DRAWINGS

The characteristic features and advantages according to the present invention will be described in more detail, in which the sole figure is a flow sheet showing an example of the method of the present invention.

DETAILED DESCRIPTION OF THE INVENTION

The method of the present invention will be described in more detail.

In the method of the present invention, diarylmethane or its derivatives are produced using an aromatic compound and a condensing agent of acetal, in which alcohol is simultaneously produced as a by-product.

Usable aromatic compounds are condensed compounds and non-condensed compounds each having a benzene ring or rings. It is necessary that the benzene ring has at least one hydrogen atom which is directly connected to the benzene ring for the condensation reaction. In addition to hydrogen atom or atoms, the benzene ring of the aromatic compound has substituent groups of alkyl group such as methyl group, ethyl group, propyl group and isopropyl group; a functional group such as hydroxyl group and aralkyl group such as benzyl group. Furthermore, the above aromatic compound may be condensed aromatic compound or its derivative such as naphthalene or methyl naphthalene. More particularly, the aromatic compound is exemplified by aromatic hydrocarbons of benzene and alkylbenzenes such as benzene, toluene, xylene, ethylbenzene, cumene, trimethybenzene, ethyltoluene, and diethylbenzene; and phenol compounds such as phenol, o-cresol and m-cresol. These compounds can be used singly or as a mixture of them. These benzene, alkylbenzenes and phenols are exemplified as preferable aromatic hydrocarbons used in the method of the present invention.

More particularly, besides the dimethoxymethane as an acetal, a high-order acetal such as bis(methoxymethyl) ether can also be used. Therefore, acetal may hereinafter include this high-order acetal.

When benzene is reacted with acetal such as dimethoxymethane, diphenylmethane is obtained. When toluene is used in place of benzene, ditolylmethane is obtained. Likewise, bis(hydroxyphenyl)methane is obtained from phenol and dimethoxymethane, and bis(hydroxymethylphenyl)methane is obtained from cresol and dimethoxymethane. When a mixture of two or more kinds of aromatic compounds are used, asymmetrical diarylmethane or its derivative can be produced. For example, when a mixture of benzene and toluene is used, phenyltolylmethane is obtained in addition to diphenylmethane and ditolylmethane.

Furthermore, by reacting benzene with dimethoxymethane under elaborately selected reaction conditions, benzyldiphenylmethane is produced as well as diphenylmethane.

The ratio of aromatic compound to acetal can be selected arbitrarily. It is desirable that the molar ratio of (aromatic compound)/(acetal) is generally in the range of 0.5 to 60. In order to improve the selectivity to diarylmethane relative to heavier substances, it is desirable that the aromatic compound is used in excess, for example, the molar ratio of (aromatic compound)/(acetal) is 2 or more.

The reaction temperature of condensation is optionally selected in the range of 80 to 400° C. If the reaction temperature is lower than 80° C., the rate of reaction is undesirably small, and in the use of some catalyst, the rate of decomposition of acetal increases as compared with the rate of reaction to produce diarylmethane or its derivatives. On the other hand, if the reaction temperature is higher than 400° C., the transalkylation of the reaction product of diarylmethane or its derivatives is caused and the yield is undesirably reduced.

There is no limit concerning the pressure of reaction, so that the pressure can be arbitrarily selected. However, if the reaction temperature is below the critical temperature of the system, the reaction pressure may be more than the vapor pressure (autogenous pressure) of reactant mixture at a reaction temperature. On the other hand, if the reaction temperature is higher than the critical temperature, it is desirable to select a pressure near the critical pressure of the system.

Concerning the mode of reaction, any of batchwise system and continuous system can be selected. In the continuous reaction, the feed rate is generally selected in the rage of 0.1 to 300 h$^{-1}$ in weight-hourly space velocity (WHSV). The range is preferably 25 to 200 h$^{-1}$. If the value of WHSV is smaller than the former range, it is not preferable because the rate of decomposition of acetal is larger than the rate of formation of intended product. If the value of WHSV is too large, it is not desirable either because the conversion rate of acetal is low. When the above-mentioned benzene, alkylbenzene and phenol are used as the desirable aromatic compounds and a continuous reaction system is employed, the value of WHSV is preferably in the range of 25 to 200 h$^{-1}$. That is, when these desirable raw materials are used in a continuous reaction system, there is a tendency that the intended product can be obtained in high a yield at relatively larger feed velocity due to the selection of reaction materials.

Reaction apparatus may be any of fluidized bed type and fixed bed type ones. The apparatus in which fixed bed reactors are connected in series can also be used.

The acid catalyst for condensation is exemplified by mineral acids such as phosphoric acid and sulfuric acid; ion exchange resin such as Amberlyst; amorphous metal oxide solid acid such as silica-alumina ($SiO_2/Al_2O_3$); and crystalline inorganic solid acid such as zeolite. The solid acid is preferable because it can be removed easily from a reaction mixture.

Among the above-mentioned solid acids, in the case of crystalline aluminosilicate catalyst having active spots in micropores, those having relatively large pore openings of ten-membered oxygen rings or larger ones are desirable. That is, the crystalline aluminosilicate catalysts having micropores of ten-membered rings or larger ones such as X-type zeolite, Y-type zeolite, L-type zeolite, mordenite, ZSM-5 (trade name, developed and sold by Mobil Oil Corp., U.S. Pat. No. 3,702,886), ZSM-11 (trade name, U.S. Pat. No. 3,709,979), ZSM-12 (trade name, U.S. Pat. No. 3,832,449) are preferable as compared with the crystalline aluminosilicate catalysts having micropores which are smaller than ten-membered rings such as erionite and ZSM-34. The crystalline aluminosilicate can be used by subjecting it to ion exchange treatment with proton, lithium ion or poly-valent cations. Furthermore, the zeolite may be used by treating it with dealuminization such as hydrothermal treatment or hydrochloric acid treatment.

It is apprehended that the catalytic activity of the condensation catalysts are impaired owing to the existence of water as described above. So that, the condensation process is preferably carried out substantially without the presence of water. For this reason, the aromatic compound and acetal as reactants are sufficiently dehydrated as occasion demands. It is preferable that the content of water in the condensation system is as small as possible, so that, when a solid acid is used as a condensation catalyst, the content of water is preferably 1,000 ppm or less in general cases.

When benzene as an aromatic compound and dimethoxymethane as acetal are used, the reaction is represented by the following equation [II]:

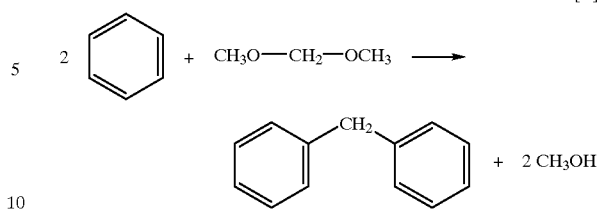

Because acetal is used as a condensing agent, alcohol is produced as a by-product and it is contained in the reaction mixture. After the condensation reaction, the catalyst is removed if necessary, to obtain a reaction mixture containing diarylmethane or its derivatives, unchanged materials of acetal and aromatic compound, and the by-product of alcohol. From this reaction mixture, the intended product of diarylmethane or its derivatives are obtained by means of separation, e.g., by distillation.

In the condensation reaction according to the present invention, a by-product of alcohol is produced as described above. When the by-product is water, it can be discarded without any undesirable influence on the cost of intended product. However, when the by-product of alcohol is generated as described above and it is discarded simply, the cost for the intended product naturally increases. In addition, the quantity of alcohol is large because two moles or more of alcohol is produced from one mole of the consumed acetal. The method of the present invention using acetal as a condensing agent have an advantage in that the reaction of condensation can be carried out substantially without the presence of water. However, as described above, if the by-product of alcohol is simply discarded, the novel method of the present invention using acetal as a condensing agent cannot be adopted in the industrial production.

However, in view of the fact that acetal as the condensing agent can be produced from alcohol and formaldehyde, if the by-product of alcohol can be recovered and reused, it is quite desirable because formaldehyde is inexpensive and the condensation reaction can be carried out without the substantial existence of water.

That is, the method of the present invention comprises the steps of: (1) preparing acetal from alcohol and formaldehyde, (2) preparing diarylmethane or its derivatives from acetal and an aromatic compound, (3) separating and recovering diarylmethane or its derivatives and alcohol from the reaction mixture of condensation, and (4) recycling at least a portion of the recovered alcohol to the initial step (1).

Each of the above processes will be described in the following.

(1) Preparation of Acetal from Alcohol and Formaldehyde

A known method in the prior art can be employed for synthesizing acetal from alcohol and formaldehyde in the presence of an acid catalyst. For example, the synthesis of acetal using a mineral acid and a Lewis acid is described in J. Frederic Waker, FORMALDEHYDE, 3rd Ed. The synthesis of acetal using an ion exchange resin catalyst is described in U.S. Pat. No. 3,248,339. Furthermore, the synthesis of acetal using a crystalline aluminosilicate of 10 or more in the molar ratio of silica to alumina is described in Japanese Patent Publication No. 62-41656.

Any of these known methods can be employed in this process. As the formaldehyde, its aqueous solution of formalin can also be used. The concentration of formalin is not limited in this invention, so that formalin of optional concentration of formaldehyde is used. Because formaldehyde is available easily in the form of an aqueous solution, i.e., formalin, so that the method of the present invention in which formalin can be used, is advantageous in economical viewpoint.

The alcohol used in the method of the present invention are aliphatic alcohols such as methanol, ethanol, n-propanol and 2-propanol; and alicyclic alcohol such as cyclohexanol. Among them, methanol is especially preferable. When methanol is used, dimethoxymethane (methylal) is obtained as acetal. In this process to produce acetal, water is generated as a by-product, so that the water content in, for example, methanol is not limited. In other words, aqueous alcohol can also be used.

The acid catalyst is not especially limited in this process. However, solid acid catalysts are preferable in view of the fact that the solid acid catalysts can easily be separated from the produced acetal. The solid acid catalysts are exemplified by acidic cation exchange resins such as sulfonated styrene-divinylbenzene copolymer and sulfonated perfluoroethylene copolymer (trade name: Nafion, made by E. I. du Pont). In addition, an inorganic solid acid such as the crystalline aluminosilicate disclosed in the foregoing Japanese Patent Publication No. 62-41656, can be used likewise.

The mode of reaction in this process may be any of batchwise reactor, flow reactor and reactive distillation system. However, reactive distillation system is preferable because the produced acetal is separated from a reaction mixture so as to caused the reaction to proceed further by shifting the equilibrium state. It is desirable to reflux in the operation of reactive distillation. The reflux ratio is not especially limited but it may be in the range of 0.1 to 30. In the flow reaction system, the liquid hourly space velocity (LHSV) is selected in the range of 0.1 to 100 $h^{-1}$.

The ratio of alcohol to formaldehyde as starting materials is optionally selected. It is generally in the range of 0.1 to 100, preferably 2 to 10, in the molar ratio of (alcohol)/(formaldehyde).

The reaction temperature in this process is generally in the range of 0 to 200° C.

After the reaction, the produced acetal is recovered by a separation method such as distillation. When dimethoxymethane is synthesized in this process, bis(methoxymethyl) ether is sometimes generated as a by-product. This by-product can also be fed to a subsequent process as a condensing agent.

In the reaction of alcohol with formaldehyde in this process, water is produced as a by-product together with acetal. When formaldehyde is fed in the form of its aqueous solution as formalin, the its water content is naturally contained in the reaction mixture. The acetal, for example, dimethoxymethane, does not form an azeotropic mixture with water. Accordingly, it is possible to separate easily the dimethoxymethane from the reaction mixture containing water and dimethoxymethane by distillation. As a result, the water content of the obtained dimethoxymethane can be maintained at a low level.

The thus obtained acetal is condensed with a separately fed aromatic compound in a succeeding process to produce diarylmethane or its derivative. In the reaction of condensation, the catalytic activity is sometimes reduced due to the existence of water. Accordingly, it is preferable to carry out the condensation without substantial existence of water. If necessary, acetal may be sufficiently dehydrated through a known method and it is fed to the next process.

(2) Preparation of Diarylmethane or its Derivatives from Acetal and Aromatic Compound In this process, diarylethane or its derivatives are produced by condensing an aromatic compound with a condensing agent of acetal prepared in the preceding process. Furthermore, alcohol is simultaneously produced as a by-product in this process. The high-order acetal of bis(methoxymethyl) ether produced in the preceding process is likewise used as a condensing agent.

Because the acetal is produced in the preceding process, the by-product of alcohol in this process is the same kind of alcohol as used in the preceding acetal preparation.

The aromatic compounds used in this process are condensed compounds or non-condensed compounds having a benzene ring or rings. It is necessary that the benzene ring has at least one hydrogen atom which is directly connected to the benzene ring. In addition to the hydrogen atom or atoms, the benzene ring of the aromatic compound may have substituent groups of alkyl group such as methyl group, ethyl group, propyl group and isopropyl group; a functional group such as hydroxyl group and aralkyl group such as benzyl group. Furthermore, the above aromatic compound may be condensed aromatic compound or its derivative such as naphthalene or methyl naphthalene. More particularly, the aromatic compound is exemplified by aromatic hydrocarbons of benzene and alkylbenzenes such as benzene, toluene, xylene, ethylbenzene, cumene, trimethybenzene, ethyltoluene, and diethylbenzene; and phenols such as phenol, o-cresol and m-cresol. These compounds can be used singly or as a mixture of them. Among them, benzene or alkylbenzene and phenols are preferable.

When benzene is reacted with acetal such as dimethoxymethane, diphenylmethane is produced. When toluene is used in place of benzene, ditolylmethane is obtained. Likewise, bis(hydroxyphenyl)methane is obtained from phenol and dimethoxymethane, and bis(hydroxymethylphenyl)methane is obtained from cresol and dimethoxymethane. When a mixture of two or more kinds of aromatic compounds are used, asymmetrical diarylmethane or its derivative can be produced. For example, a mixture of benzene and toluene is used, phenyltolylmethane is obtained in addition to diphenylmethane and ditolylmethane.

Furthermore, by reacting benzene with dimethoxymethane under suitably selected reaction conditions, benzyl-diphenylmethane is produced as well as diphenylmethane.

The ratio of aromatic compound to acetal can be selected optionally. It is preferable that the molar ratio of (aromatic compound)/(acetal) is generally in the range of 0.5 to 60. In order to improve the selectivity to diarylmethane relative to heavier substances, it is desirable that the aromatic compound is used in excess, for example, the molar ratio of (aromatic compound)/(acetal) is 2 or more.

The reaction temperature of condensation in this process is optionally selected in the range of 80 to 400° C. If the reaction temperature is lower than 80° C., the rate of reaction is undesirably small, and in the use of some catalyst, the rate of decomposition of acetal increases as compared with the rate of reaction to produce diarylmethane or its derivatives. On the other hand, if the reaction temperature is higher than 400° C., the transalkylation of the reaction product of diarylmethane or its derivatives is caused and the yield is undesirably reduced.

There is no limit concerning the pressure of reaction, so that the pressure can be arbitrarily selected. However, if the reaction temperature is lower than the critical temperature of the reaction system, the reaction pressure may be more than the vapor pressure (autogenous pressure) of reactant mixture at a reaction temperature. On the other hand, if the reaction temperature is higher than the critical temperature, it is desirable to select a pressure near the critical pressure of the system.

Concerning the mode of reaction, any of batchwise system and continuous system can be selected. In continuous reaction, the feed rate is generally selected in the rage of 0.1 to 300 $h^{-1}$ in weight-hourly space velocity (WHSV). The range is preferably 25 to 200 $h^{-1}$. If the value of WHSV is smaller than the former range, it is not preferable because the rate of decomposition of acetal is larger than the rate of formation of intended product. If the value of WHSV is too large, it is not desirable either because the conversion rate of acetal is low. When the above-mentioned benzene, alkylbenzene and phenol are used as the desirable aromatic compounds and a continuous reaction system is employed, the value of WHSV is preferably in the range of 25 to 200 $h^{-1}$. That is, when these desirable raw materials are used in a continuous reaction system, there is a tendency that the intended product can be obtained in high yield at relatively larger feed velocity due to the selection of reaction materials.

Reaction apparatus may be any of fluidized bed type and fixed bed type ones. The apparatus in which fixed bed reactors are connected in series can also be used.

The acid catalyst for condensation is exemplified by mineral acids such as phosphoric acid and sulfuric acid; an ion exchange resin such as Amberlyst; an amorphous metal oxide solid acid such as silica-alumina ($SiO_2/Al_2O_3$); and a crystalline inorganic solid acid such as zeolite. The solid acid is preferable because it can be removed easily from a reaction mixture.

Among the above-mentioned solid acids, in the case that crystalline aluminosilicate catalyst having active spots in micropores is used, those having relatively large pore openings of ten-membered oxygen rings or larger ones are desirable. That is, the crystalline aluminosilicate catalysts having micropores of ten-membered rings or larger ones such as X-type zeolite, Y-type zeolite, L-type zeolite, mordenite, ZSM-5 (trade name, developed and sold by Mobil Oil Corp., U.S. Pat. No. 3,702,886), ZSM-11 (trade name, U.S. Pat. No. 3,709,979), ZSM-12 (trade name, U.S. Pat. No. 3,832,449) are preferable as compared with the crystalline aluminosilicate catalysts having micropores of smaller than ten-membered rings such as erionite and ZSM-34. The crystalline aluminosilicate can be used by subjecting ion exchange with proton, lithium ion or polyvalent cations. Furthermore, the zeolite may be used by subjected it to dealuminization such as hydrothermal treatment or hydrochloric acid treatment.

After the reaction, the intended product of diarylmethane or its derivatives are obtained from the reaction mixture through an appropriate method such as distillation.

It is apprehended that the catalytic activity of the condensation catalysts are impaired owing to the existence of water as described above. So that, the condensation process is preferably carried out substantially without the presence of water. For this reason, the aromatic compound and acetal as reactants are sufficiently dehydrated as occasion demands. The content of water in the condensation system is made as small as possible. When a solid acid is used as a condensation catalyst, the content of water is preferably 1,000 ppm or less in general cases.

Because acetal is used as a condensing agent in this process, alcohol is produced as a by-product. So that, alcohol is contained in the reaction mixture. After the reaction, the catalyst is removed as occasion demands to obtain a reaction mixture containing diarylmethane or its derivatives, unchanged raw materials of acetal and aromatic compound, and the by-product of alcohol. This reaction mixture is fed to the next process.

(3) Separation and Recovery of Diarylmethane or its Derivatives and Alcohol from the Condensation Reaction Mixture It is the object of this process to recover the intended product of diarylmethane or its derivatives and alcohol as a by-product simultaneously. The alcohol is reused in the next process as a raw material for producing acetal.

Any suitable method can be employed for separating and recovering the produced diarylmethane or its derivatives and alcohol, respectively. For example, any one of separation means such as distillation, extractive distillation, extraction and oil-water separation can be selected in accordance with the composition of reaction mixture.

For example, when an aromatic compound of benzene or toluene is condensed with dimethoxymethane, the reaction mixture containing alcohol is extracted with water, and an aqueous phase containing alcohol is separated by oil-water separation. From this phase, alcohol is easily recovered, for example, by distillation. In the case that an aqueous solution of formaldehyde is used in the process (1), the aqueous phase is preferably recycled as it stands without the removal of water from alcohol in this process.

From the oily phase which is obtained in the oil-water separation, the intended product of diarylmethane or its derivatives are obtained through an appropriate separation method such as distillation. The distillation may be any of reduced pressure distillation and atmospheric pressure distillation.

When phenol is condensed with dimethoxymethane, unreacted phenol is soluble to water, so that the extraction with water is not desirable. In this case, it is preferable that the intended product of diarylmethane or its derivatives and by-product of alcohol are separated and recovered from the above-mentioned reaction mixture by means of distillation.

(4) Recycling of Recovered Alcohol to Process (1)

In this process, at least a part of or preferably the whole of the alcohol recovered in the preceding process (3), is recycled to the process (1) to be reused as a reactant. When an aqueous solution of formaldehyde is used in the process (1) as described above, it is desirable that the alcohol is not separated from the aqueous phase and the recovered aqueous alcohol is recycled intact to the process (1). Of course, it is also possible to use the alcohol by adjusting its water content properly if desired.

By recycling the recovered by-product alcohol as a feed material for the process (1) without discarding it, the whole of the alcohol can be reused, as a result, the raw material cost can be reduced.

In the following, a preferred embodiment of the method of the present invention will be described with reference to the accompanying drawing.

The Figure is a flow sheet showing an example of the process according to the present invention, in which dimethoxymethane is prepared from methanol and formaldehyde, and benzene is condensed with dimethoxymethane to produce diphenylmethane. At the same time, methanol as a by-product is reused by recycling.

In the first place, an aqueous solution of formaldehyde is fed from a line 1 and methanol is fed from lines 2 and 9. These materials are combined and fed to a reactive distillation column 3. While reacting these materials in the reactive distillation column 3, the operation of distillation is carried out simultaneously to obtain dimethoxymethane.

The reactive distillation column 3 is provided with a refluxing device (not shown). Its reflux ratio is set to, for example, 10. By the way, the reactive distillation column 3 is filled in advance with a catalyst, for example, an ion exchange resin.

The methanol in line 9 is a material which is obtained in the below-described recovery process. The methanol in line 2 is a starting material or an additionally fed material. Accordingly, in a regular state of operation, the methanol is mainly fed from the line 9.

In the reactive distillation column 3, distillation is continuously done while causing the reaction and dimethoxymethane is taken out through a line 4 from the top of the column 3 and the by-product water and the water contained in the feed of aqueous solution of formaldehyde are taken out from the bottom of the column. The whole of water from the bottom of column can be discharged through a line 10. In the process shown on FIG. 1, a part of water is fed to an oil-water separator 11 through a line 8 as an extraction solvent used in the oil-water separation process as described later.

In the next step, the above-mentioned dimethoxymethane (through line 4) and benzene which is separately fed through a line 5, are fed to a flow-type fixed bed reactor 6 to carry out condensation so as to produce diphenylmethane. In this reaction, diphenylmethane is produced together with a by-product of methanol. The fixed bed of the reactor 6 comprises, for example, a silica-alumina catalyst. The reaction temperature may be, for example, 250° C. and the reaction pressure may be an autogenous pressure.

The reaction mixture (diphenylmethane and the by-product of methanol) derived from the fixed bed reactor 6 through the line 7 is combined with water from the reactive distillation column 3 through the line 8 and it is fed to an oil-water separator 11. It is possible to add water to the reactant liquid using a stirrer such as an optional mixer (not shown) so as to mix together sufficiently.

In the oil-water separator 11, the above-mentioned mixed liquid is separated into an organic phase (oily phase) containing diphenylmethane and aqueous phase containing methanol. A known apparatus can be used as the oil-water separator. For example, a vessel in which the reaction mixture (through line 7) and water (through line 8) are sufficiently mixed together continuously and then they are settled to separate, can be used.

Because an aqueous solution of formaldehyde is fed to the above-mentioned reactive distillation column 3, the separated methanol containing water is recycled intact through a line 9 to the initial acetal preparation step of the reactive distillation column 3 without removing water contained therein. In this process, according to the reaction conditions in the reactive distillation column 3, it is also possible to control the operation by regulating the water content of recycled methanol. It is convenient for the operation because the alcohol recycled to the reactive distillation column 3 can contain a certain amount of water with the use of an aqueous solution of formaldehyde in the reactive distillation column 3.

In the next step, the oily phase containing diarylmethane which is separated in the oil-water separator 11, is fed to a distillation column 13 through a line 12. The intended product of diarylmethane is taken out from the bottom of the column 13 through a line 14. Unchanged benzene is taken out from the top of distillation column 13. Because this benzene is excessively fed relative to the amount of dimethoxymethane, the quantity of unchanged benzene is comparatively large. Therefore, in the process as shown in FIG. 1, the benzene taken out from the distillation column 13 is recycled to the fixed bed reactor 6 as a part of reactant for the condensation, thereby attaining the efficient use of the unchanged benzene.

The present invention will be described in more detail with reference to several preparation examples. In the following description, "%" means "% by weight" unless otherwise indicated.

In Examples 1 to 4 and Comparative Example, the condensation reaction in the foregoing step (2) was carried out independently. In Example 5, the whole of the foregoing steps (1) to (3) were carried out totally. Meanwhile, in Example 6, the foregoing steps (2) and (3) were carried out using the reaction product of acetal preparation process in Example 5.

EXAMPLE 1

2.6 g of a commercially available silica-alumina catalyst (trade name: N 632 L, made by Nikki Chemical Corp.), 78 g of benzene, and 7.6 g of dimethoxymethane (chemical reagent grade, made by Kishida Chemical Co., Ltd.) were fed to a 300 ml autoclave (made by Nitto Koatsu K.K.) equipped with a stirrer and the contents were stirred at 250° C. for 1 hour. When the reaction was finished, the pressure in the autoclave was 34 atm at 250° C.

It was confirmed by gas chromatographic analysis of the reaction mixture that the rate of conversion of dimethoxymethane was 96.1% and the content of diphenylmethane in the reaction mixture was 7.2%.

EXAMPLE 2

2.6 g of a commercially available mordenite catalyst (trade name: HSZ 690 NOA, made by Tosoh Corp.), 78 g of benzene, and 7.6 g of dimethoxymethane were fed to a 300 ml autoclave (made by Nitto Koatsu K. K.) equipped with a stirrer and the contents were stirred at 250° C. for 1 hour. When the reaction was finished, the pressure in the autoclave was 32 atm at 250° C.

It was confirmed by gas chromatographic analysis of the reaction mixture that the rate of conversion of dimethoxymethane was 98.3% and the content of diphenylmethane in the reaction mixture was 10.3%.

EXAMPLE 3

3 g of a commercially available mordenite catalyst (trade name: HSZ 690 NOA, made by Tosoh Corp.), 92 g of toluene, and 7.6 g of dimethoxymethane were fed to a 300 ml autoclave (made by Nitto Koatsu K. K.) equipped with a stirrer and the contents were stirred at 250° C. for 1 hour. When the reaction was finished, the pressure in the autoclave was 26 atm at 250° C.

It was confirmed by gas chromatographic analysis of the reaction mixture that the rate of conversion of dimethoxymethane was 95.6% and the content of ditolylmethane the reaction mixture was 13.4%.

EXAMPLE 4

A stainless steel tube of 6 mm in inner diameter was filled with 3 g of a commercially available mordenite catalyst (trade name: HSZ 690 NOA, made by Tosoh Corp.) and it was heated to 250° C. with a tubular electric heater. Then, liquid phase reaction was carried out by feeding 9.7% solution of dimethoxymethane in benzene at a rate of 120 g/hr under a pressure of 60 atm using a metering pump. The value in WHSV was 40 $h^{-1}$.

It was confirmed by gas chromatographic analysis of the reaction mixture that the rate of conversion of dimethoxymethane was 96.8% and the content of diphenylmethane in the reaction mixture was 10.3%.

Comparative Example 2.6 g of a commercially available silica-alumina catalyst (trade name: N 632 L, made by Nikki Chemical Corp.), 78 g of benzene, and 4.1 g of formaldehyde solution (chemical reagent grade 37% solution, made by Kishida Chemical Co., Ltd.) were fed to a 300 ml autoclave (made by Nitto Koatsu K. K.) equipped with a stirrer and the contents were stirred at 250° C. for 3 hours. The pressure in the autoclave was 38 atm at 250° C.

It was confirmed by gas chromatographic analysis of the reaction mixture that the rate of conversion of formaldehyde was 20.1% and the content of diphenylmethane in the reaction mixture was 2.0%.

EXAMPLE 5

(1) Preparation of Acetal from Alcohol and Formaldehyde

To a 300 ml round bottom flask having a refluxing device are fed 100 g of formalin (37% formaldehyde conc.), 79 g of methanol and 1.11 g of a catalyst of strong cation exchange resin (trade name: Amberlyst 15, made by Organo Corp.) Reactive distillation was done with stirring and heating. After refluxing of the whole contents for 30 minutes, collection of distillate was started at a reflux ratio of 10 and the quantity of distillate was 60 g per 1 hour. The distillate was composed of 92% of dimethoxymethane and 8% of methanol.

(2) Preparation of Diarylmethane or its Derivative from Acetal and Aromatic Compound 2.6 g of a commercially available silica-alumina catalyst (trade name: N 632 L, made by Nikki Chemical Corp.), 78 g of benzene, and 7.6 g of a mixture of dimethoxymethane and methanol which was obtained in the preceding step were fed to a 300 ml autoclave (made by Nitto Koatsu K.K.) equipped with a stirrer and the contents were stirred at 250° C. for 1 hour. The content of water in this reaction system was 200 ppm. When the reaction was finished, the pressure in the autoclave was 34 atm at 250° C.

It was confirmed by gas chromatographic analysis of the reaction mixture that the rate of conversion of dimethoxymethane was 91.8% and the content of diphenylmethane was 5.7% and methanol was 3.0% in the reaction mixture.

(3) Recovery of Alcohol 80 g of the reaction mixture obtained in the preceding step and 8 g of distilled water were fed to a 300 ml separating funnel and extraction of methanol was done by shaking it sufficiently. By analysis, it was confirmed that 25% of methanol was contained in an aqueous phase which was obtained by settling. Further, diphenylmethane was obtained by ordinarily distilling the separated oily phase containing diphenylmethane.

Using 8 g of the recovered 25% methanol aqueous phase and 2.5 g of formalin containing 37% of formaldehyde, the reactive distillation was carried out in the like manner as the foregoing acetal preparation step (1) to obtain a distillate containing 92% of dimethoxymethane and 8% of methanol. Accordingly, it was confirmed that the recovered methanol solution can be used as a methanol source for the above-mentioned acetal preparation step.

EXAMPLE 6

3 g of a commercially available silica-alumina catalyst (trade name: N 632 L, made by Nikki Chemical Corp.), 94 g of phenol and 7.6 g of a mixture of dimethoxymethane and methanol which was obtained in Example 5 were fed to a 300 ml autoclave (made by Nitto Koatsu K.K.) equipped with a stirrer and the contents were stirred at 250° C. for 1 hour. When the reaction was finished, the pressure in the autoclave was 8 atm at 250° C.

It was confirmed by gas chromatographic analysis of the reaction mixture that the rate of conversion of dimethoxymethane was 98.8% and the content of bis(hydroxyphenyl)methane was 12.7 and methanol was 2.6% in the reaction mixture.

The obtained reaction mixture was subjected to ordinary distillation to obtain 1.8 g of methanol and bis(hydroxyphenyl)methane.

Using 1.8 g of the recovered methanol and 2.3 g of formalin containing 37% of formaldehyde, the reactive distillation was carried out in the like manner as the foregoing acetal preparation step (1) in Example 5 to obtain a distillate containing 92% of dimethoxymethane and 8% of methanol. Accordingly, it was confirmed that the recovered methanol solution can be used as a methanol source for the above-mentioned acetal preparation step.

DISCUSSION

In the conventional condensation of an aromatic compound with formaldehyde in the presence of an acid catalyst, the catalyst suffers undesirable influence because water is produced in the reaction. However, in the method of the present invention, alcohol is produced in place of water having undesirable influence on the catalyst, so that it is possible to carry out the condensation under the condition without substantial existence water and the undesirable influence on the catalyst can be eliminated. In addition, because the by-product of alcohol can be reused, the method of the present invention is very advantageous as compared with the conventional methods.

That is, in the conventional method, water is generated and it was only discarded. In the method of the present invention, acetal is used as a condensing agent and alcohol as a by-product is recovered and it is advantageous in that the recovered alcohol can be reused as a material for preparing acetal.

In the method of the present invention, acetal is produced from formaldehyde and alcohol and diarylmethane or its derivatives are produced from the acetal and an aromatic compound. In this preparation process, the alcohol is once consumed in a reaction system and it is released in the next step. The method like this can provide an epoch-making advantages. Furthermore, the series of reaction can be carried out at low cost without difficulty.

In addition, because the acetal does not form an azeotropic mixture with water, even though water is generated in the acetal formation, it is possible to obtain the acetal which scarcely contain water and the acetal is used in the next process. As a result, the condensation reaction of aromatic compound with the acetal can be carried out under the condition substantially containing no water.

What is claimed is:

1. A method for producing a diarylmethane comprising the following steps of (1) to (4):

(1) reacting an alcohol with formaldehyde in the presence of an acid catalyst to obtain an acetal;

(2) reacting the acetal and an aromatic compound in the presence of a solid acid catalyst selected from amorphous metal oxide solid acids or crystalline inorganic solid acids to obtain a reaction mixture containing a diarylmethane and an alcohol;

(3) separating and recovering the diarylmethane and the alcohol from said reaction mixture containing the diarylmethane and alcohol; and (4) recycling at least a portion of said recovered alcohol to said step (1) for acetal preparation.

2. The method as claimed in claim 1 wherein an aqueous solution of formaldehyde is used as said formaldehyde in said step (1), and the reaction mixture in said step (3) is extracted with water to separate the mixture into an oily phase and an aqueous phase, then, said diarylmethane is recovered from said oily phase, said alcohol is recovered from said aqueous phase, and at least a part of said alcohol is recycled to said step (1).

3. The method as claimed in claim 1 wherein said separating and recovering operation in said step (3) is done by distillation.

4. The method as claimed in claim 1 wherein said alcohol in said step (1) is methanol and said acetal is dimethoxymethane.

5. The method as claimed in claim 1 wherein said aromatic compound in said step (2) is benzene and/or toluene.

6. The method as claimed in claim 1 wherein said aromatic compound in said step (2) is phenol and/or cresol.

7. The method as claimed in claim 1 wherein said reaction of alcohol with formaldehyde in said step (1) is done by reactive distillation.

8. The method as claimed in claim 2 wherein said alcohol in said step (1) is methanol and said acetal is dimethoxymethane.

9. The method as claimed in claim 3 wherein said alcohol in said step (1) is methanol and said acetal is dimethoxymethane.

10. The method as claimed in claim 2 wherein said aromatic compound in said step (2) is benzene and/or toluene.

11. The method as claimed in claim 3 wherein said aromatic compound in said step (2) is benzene and/or toluene.

12. The method as claimed in claim 2 wherein said aromatic compound in said step (2) is phenol and/or cresol.

13. The method as claimed in claim 3 wherein said aromatic compound in said step (2) is phenol and/or cresol.

14. A method as claimed in claim 1, wherein said diarylmethane is represented by the formula [I]

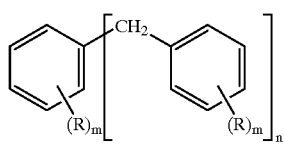

[I]

wherein m is an integer from 0 to 3, n is 1 or 2, and each R is the same or different and is selected from hydrogen, alkyl groups having from 1 to 4 carbon atoms.

15. The method as claimed in claim 1 wherein said aromatic compound is benzene.

16. The method as claimed in claim 1 wherein said aromatic compound is toluene.

17. A method for producing a compound represented by the formula

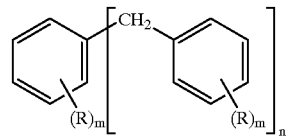

[I]

wherein m is an integer from 0 to 3, n is 1 or 2, and each R is the same or different and is selected from hydrogen or alkyl groups having from 1 to 4 carbon atoms;

comprising reacting dimethoxymethane and/or bis(methoxymethyl)ether with an aromatic compound selected from benzene or alkyl substituted benzenes at a reaction temperature in the range of 80° C. to 400° C. in the presence of an acid catalyst selected from amorphous metal oxide solid acids or crystalline inorganic solid acids.

18. The method as claimed in claim 17 wherein said aromatic compound is benzene.

19. The method as claimed in claim 17 wherein said aromatic compound is toluene.

20. A method as claimed in claim 17 wherein said acid catalyst is a crystalline inorganic solid and is selected from crystalline aluminosilicate catalysts having micropores of ten-membered rings or larger comprising at least one zeolite.

21. A method as claimed in claim 17, wherein the content of water in the reaction system is 1,000 ppm or less.

22. A method as claimed in claim 17, wherein the reacting of dimethoxymethane and/or bis(methoxymethyl) ether with an aromatic compound is conducted at a reaction pressure equal to or greater than the vapor pressure or near the critical pressure of the system.

23. The process of claim 1 wherein the solid acid catalyst is selected from amorphous metal oxide solid acids or crystalline aluminosilicate catalysts.

24. The process of claim 17 wherein the solid acid catalyst is selected from amorphous metal oxide solid acids or crystalline aluminosilicate catalysts.

* * * * *